US008406873B2

United States Patent
Sauer et al.

(10) Patent No.: US 8,406,873 B2
(45) Date of Patent: Mar. 26, 2013

(54) METHODS AND SYSTEMS FOR IMPLEMENTING A HIGH VOLTAGE SWITCHING CIRCUIT IN AN IMD

(75) Inventors: Christian Sauer, Cupertino, CA (US); Jeff Alves, Sunnyvale, CA (US); Gabriel A. Mouchawar, Valencia, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 149 days.

(21) Appl. No.: 13/018,736

(22) Filed: Feb. 1, 2011

(65) Prior Publication Data
US 2012/0197325 A1   Aug. 2, 2012

Related U.S. Application Data

(63) Continuation-in-part of application No. 13/018,036, filed on Jan. 31, 2011, now abandoned.

(51) Int. Cl.
*A61N 1/00* (2006.01)

(52) U.S. Cl. ............................................. 607/5; 607/2
(58) Field of Classification Search ............... 607/2, 4–5
See application file for complete search history.

(56) References Cited

U.S. PATENT DOCUMENTS

| | | | |
|---|---|---|---|
| 8,116,865 B2* | 2/2012 | Linder et al. | 607/5 |
| 8,209,005 B1* | 6/2012 | Moulder et al. | 600/547 |
| 8,209,007 B2* | 6/2012 | McIntyre et al. | 607/5 |
| 2002/0072769 A1* | 6/2002 | Silvian et al. | 607/2 |

\* cited by examiner

*Primary Examiner* — Christopher D Koharski
*Assistant Examiner* — Catherine Voorhees
(74) *Attorney, Agent, or Firm* — Theresa Ann Raymer; Steven M. Mitchell

(57) ABSTRACT

A high voltage switching and control circuit is provided for an implantable medical device (IMD). The circuit includes a high voltage positive (HVP) node, configured to receive a positive high voltage signal from a high energy storage source, and a high voltage negative (HVN) node, configured to receive a negative high voltage signal from a high energy storage source. Additionally, the circuit includes first, second and third output terminals that are configured to be connected to electrodes for delivering high voltage energy. First and second SCR switches are connected to the first and second output terminals, respectively. The first and second SCR switches are connected in series with one another and are connected to one of the HVP and HVN nodes. The first and second SCR switches have gating terminals. A control circuit is connected to the gating terminals and delivers first and second gating signals to turn ON the first and second SCR switches, respectively. The control circuit temporally offsets the first and second gating signals to turn ON the first and second SCR switches in a serial delayed manner.

19 Claims, 7 Drawing Sheets

METHODS AND SYSTEMS FOR IMPLEMENTING A HIGH VOLTAGE SWITCHING CIRCUIT IN AN IMD

CROSS-REFERENCE TO RELATED APPLICATIONS

The present application is a continuation-in-part of U.S. application Ser. No. 13/016,036, filed Jan. 31, 2011, and entitled "Methods and Systems for Implementing A High Voltage Switching Circuit in an IMD," now abandoned, which is hereby incorporated by reference in its entirety.

BACKGROUND OF THE INVENTION

Embodiments are described herein that relate generally to medical devices for treating various cardiac, physiologic and neurologic disorders. More particularly, embodiments are described that relate to implantable or external medical devices with a high voltage delivery circuit.

Numerous medical devices exist today, including but not limited to electrocardiographs ("ECGs"), electroencephalographs ("EEGs"), squid magnetometers, implantable pacemakers, implantable cardioverter-defibrillators ("ICDs"), neurostimulators, electrophysiology ("EP") mapping and radio frequency ("RF") ablation systems, and the like (hereafter generally "implantable medical devices" or "IMDs"). IMDs commonly employ one or more leads with electrodes that either receive or deliver voltage, current or other electromagnetic pulses (generally "energy") from or to an organ or tissue (collectively hereafter "tissue") for diagnostic or therapeutic purposes.

Certain types of IMDs include internal charge storage members, such as one or more capacitors. The charge storage members are connected to a switch circuit or network also referred to as an H-bridge. Conventional high voltage H-bridges include a network of transistors that are controlled to open and close in different combinations to deliver stored energy from the charge storage members to a patient through the electrodes. Heretofore, the H-bridge circuits in IMDs have used switches implemented through IGBTs (Insulated Gate Bipolar Transistors). An IGBT is a three-terminal power semiconductor device. However, IGBTs are relatively large and somewhat expensive.

Another type of switch device used in other electronic fields is a Silicon Controlled Rectifier (SCR). SCRs are smaller in size and less expensive than IGBTs. However, SCRs exhibit different operational characteristics than IGBTs. SCRs are latching devices, and thus once triggered an SCR switch will stay ON as long as current is flowing through the SCR. In other words, once an SCR switch is turned ON, it stays in the ON state while current is flowing. In the case of a high voltage delivery circuit, the voltage potential across an SCR switch exceeds the operating voltage of the switch's control circuit, Therefore, in a conventional H-bridge circuit if one of the SCR switches triggers before the other, a high voltage potential is created across the cathode of the un-triggered SCR switch. This high voltage potential exceeds the maximum operating voltage of the control circuit. Hence, the control circuit cannot generate enough voltage to drive current into the gate of the un-triggered SCR. Therefore, the control circuit fails to close the un-triggered SCR switch. Therefore, if a high voltage potential is created across an SCR switch while in an OFF state, the SCR switch cannot be changed to an ON state, Thus, an SCR switch exhibits more limited operational control as compared to other types of switches such as IGBT switches.

SCR switches are not readily substituted for IGBT switches in a high voltage H-bridge circuit, because the bridge circuit experiences certain operational difficulties when SCR switches are implemented. In many IMDs today, the high voltage bridge circuit includes three output terminals that are configured to be coupled to three separate electrodes capable of delivering high voltage energy to a patient. A network of six IGBT switches connects the output terminals to a high voltage positive (HVP) source and a high voltage negative (HVN) source. Each output terminal is located between, and in series with, corresponding pair of IGBT switches that are located between the HVP and HVN sources. One of each pair of IGBT switches open and close to connect or disconnect the corresponding output terminal, to one of the HVP and HVN sources.

SCR switches cannot be directly substituted for IGBT switches into a traditional H-bridge architecture because the latching behavior characteristic of the SCR switches adds a design complexity. For example, if a pair of output terminals are to be connected in parallel to the HVP sources, the risk exists that the SCR switches for one of the output terminal pair turns ON before the SCR switch for the second of the output terminal pair. When the first SCR switch turns ON, current begins to flow to the patient, thereby creating a voltage potential higher than the maximum voltage of the control circuit at the cathode of the second SCR switch. Once a voltage potential is created on the cathode of the second SCR switch, it stays in its initial state, namely OFF. Hence, the control circuit is not able to turn ON the second SCR switch and one of the two output terminals does not deliver a high energy shock.

Instead, the SCR switches should be opened simultaneously. However, opening the SCR switches simultaneously is not practical given the operational tolerances of the SCR devices and surrounding components.

Accordingly, a need remains for an improved high voltage H-bridge circuit that is able to realize the benefits of SCR switches without introducing the risks associated with the latching behavior of SCR switches.

SUMMARY

In accordance with one embodiment, a high voltage switching and control circuit is provided for an implantable medical device (IMD). The circuit includes a high voltage positive (HVP) node, configured to receive a positive high voltage signal from a high energy storage source, and a high voltage negative (HVN) node, configured to receive a negative high voltage signal from a high energy storage source. Additionally, the circuit includes first, second and third output terminals that are configured to be connected to electrodes for delivering high voltage energy. First and second SCR switches are connected to the first and second output terminals, respectively. The first and second SCR switches are connected in series with one another and are connected to one of the HVP and HVN nodes. The first and second SCR switches have gating terminals. A control circuit is connected to the gating terminals and delivers first and second gating signals to turn ON the first and second SCR switches, respectively. The control circuit temporally offsets the first and second gating signals to turn ON the first and second SCR switches in a serial delayed manner.

In accordance with one embodiment, a method is provided for operating a high voltage switching and control circuit in an IMD. The method includes providing HVP and negative HVN nodes. The method further provides first, second and third output terminals configured to be connected to electrodes for delivering high voltage energy. Additionally, the method provides multiple switches connecting the HVP and HVN nodes to the first, second and third output terminals. The switches including at least first and second SCR switches connected in series with one another and connected to one of the HVP and HVN nodes. The first and second SCR switches have gating terminals, and an input of the second SCR switch being connected to an output of the first SCR switch. The method further comprises providing high voltage signals from a high energy storage source at the HVP node and the HVN node. The method delivers a second gating signal to the gating terminal of the second SCR switch to turn ON the second SCR switch. The method also includes delivering a first gating signal to the gating terminal of the first SCR switch to turn ON the first SCR switch.

The method offsets delivery timing of the first and second gating signals in a serial delayed manner such that the second gating signal turns ON the second SCR switch before the first gating signal turns ON the first SCR switch. Additionally, the method includes delivering high voltage energy to the first and second output terminals at substantially a common time in response to the first gating signal turning ON the first SCR switch.

DETAILED DESCRIPTION

Figure 1:
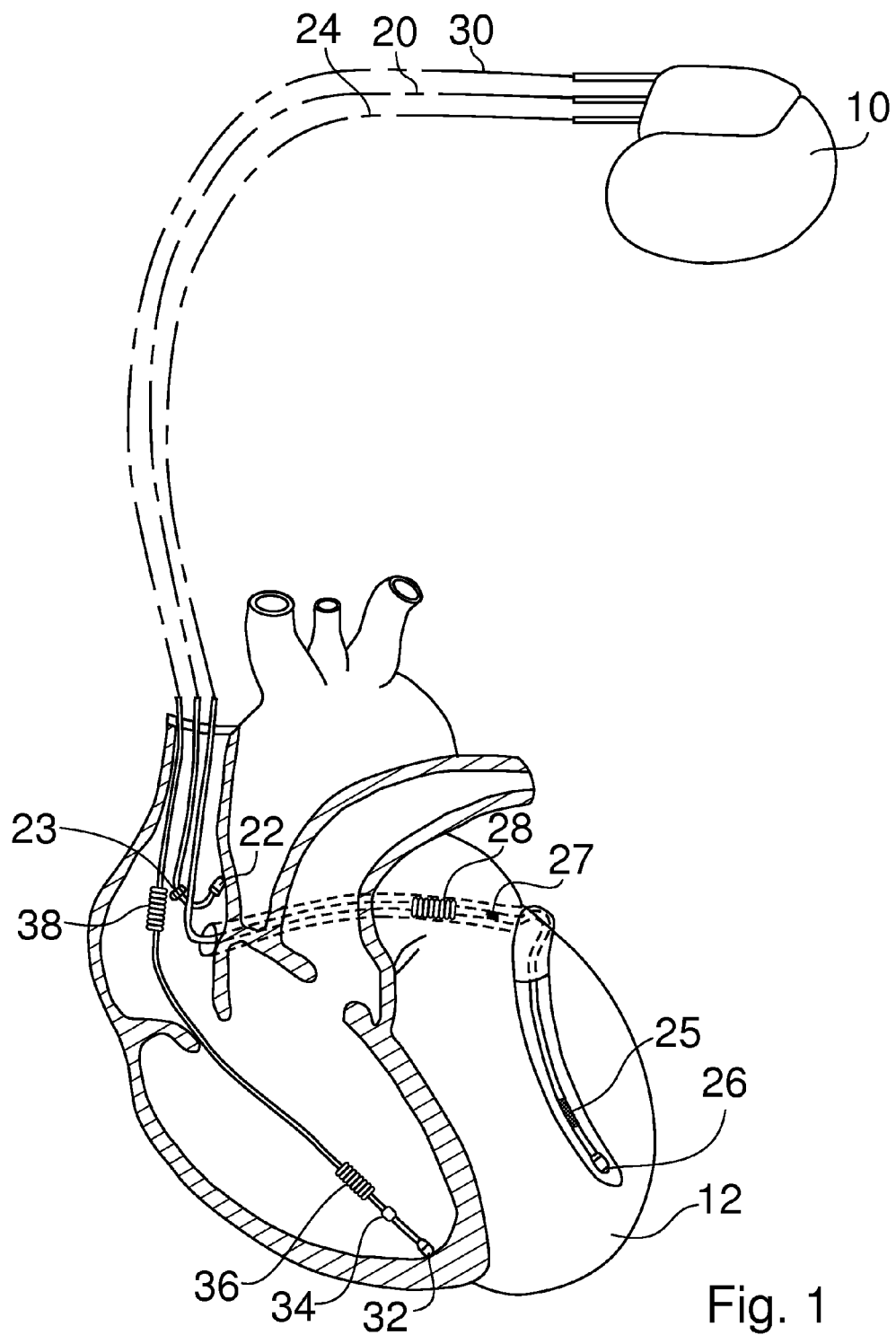
FIG. 1 is a simplified view of an exemplary implantable medical device (IMD) in electrical communication with at least three leads implanted into a patient's heart in accordance with an embodiment.

FIG. 1 illustrates an IMD 10 in electrical communication with a patient's heart 12 by way of three leads 20, 24 and 30 suitable for delivering multi-chamber stimulation and/or shock therapy. To sense atrial cardiac signals and to provide right atrial chamber stimulation therapy, the IMD 10 is coupled to an implantable right atrial lead 20 including at least one atrial tip electrode 22 that typically is implanted in the patient's right atrial appendage. The right atrial lead 20 may also include an atrial ring electrode 23 to allow bipolar stimulation or sensing in combination with the atrial tip electrode 22.

To sense the left atrial and left ventricular cardiac signals and to provide left-chamber stimulation therapy, the IMD 10 is coupled to a "coronary sinus" lead 24 designed for placement in the "coronary sinus region" via the coronary sinus ostium in order to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to: receive atrial and/or ventricular cardiac signals; deliver left ventricular pacing therapy using at least one left ventricular tip electrode 26 for unipolar configurations or in combination with left ventricular ring electrode 25 for bipolar configurations; deliver left atrial pacing therapy using at least one left atrial ring electrode 27 as well as shocking therapy using at least one left atrial coil electrode 28.

The IMD 10 is also shown in electrical communication with the patient's heart 12 by way of an implantable right ventricular lead 30 including, in the embodiment, a right ventricular (RV) tip electrode 32, a right ventricular ring electrode 34, a right ventricular coil electrode 36, a superior vena cava (SVC) coil electrode 38, and so on. Typically, the right ventricular lead 30 is inserted transvenously into the heart 12 so as to place the right ventricular tip electrode 32 in the right ventricular apex such that the RV coil electrode 36 is positioned in the right ventricle and the SVC coil electrode 38 will be positioned in the right atrium and/or superior vena cave. Accordingly, the right ventricular lead 30 is capable of receiving cardiac signals, and delivering stimulation in the form of pacing and shock therapy to the right ventricle.

Figure 2:
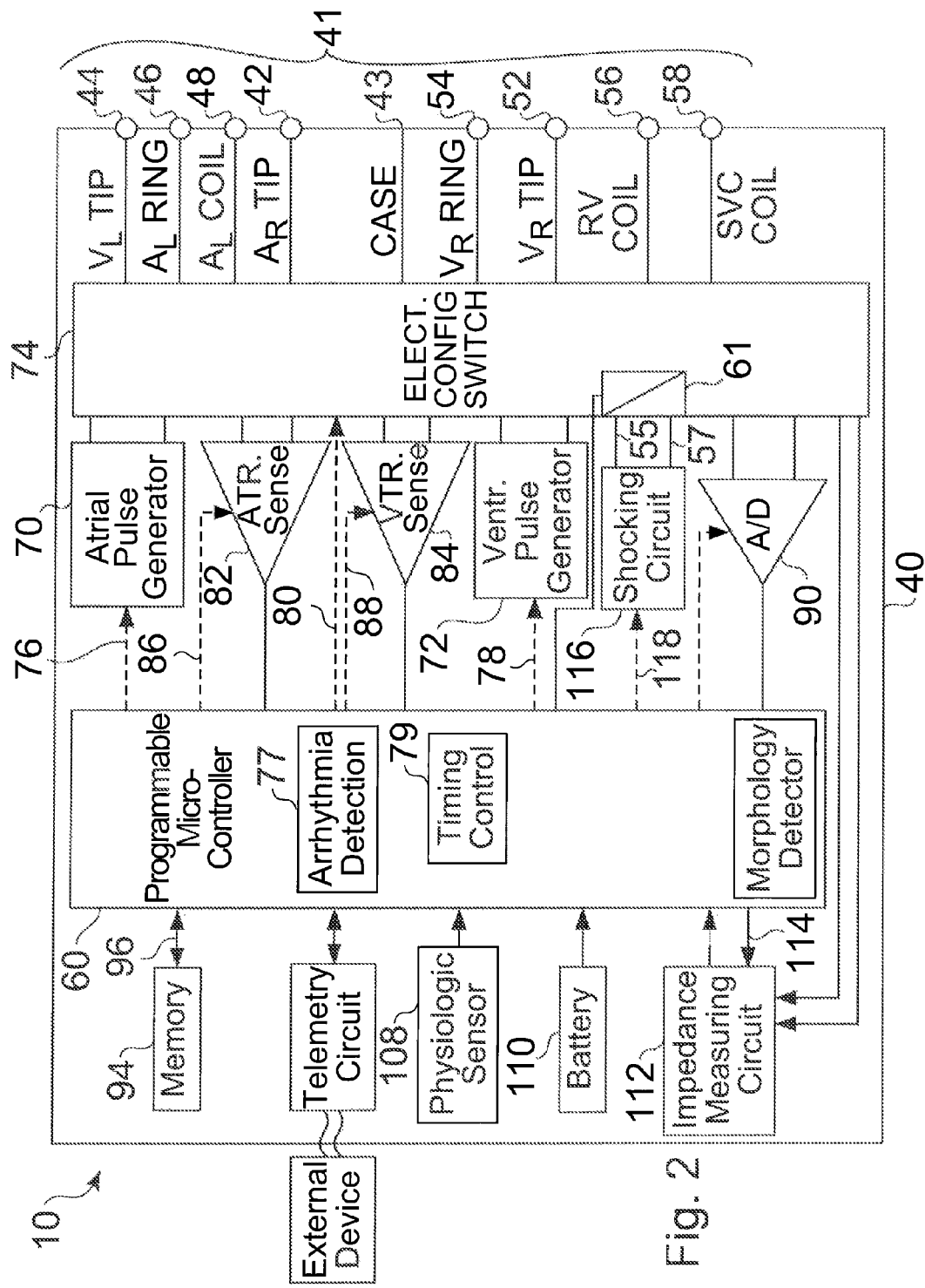
FIG. 2 is a functional block diagram of the IMD of FIG. 1.

FIG. 2 illustrates a simplified block diagram of the multi-chamber IMD 10, which is capable of treating both fast arrhythmia and slow arrhythmia with stimulation therapy, including cardioversion, defibrillation, and pacing stimulation. While a particular multi-chamber device is shown, the multi-chamber device is for illustration purposes only, and one of ordinary skill in the pertinent art could readily duplicate, eliminate or disable the appropriate circuitry in any desired combination to provide a device capable of treating the appropriate chamber(s) with cardioversion, defibrillation, and/or pacing stimulation.

The IMD 10 includes a housing 40 which is often referred to as "can," "case," or "case electrode," and which may be programmably selected to act as the return electrode for all "unipolar" modes. The housing 40 may further be used as a return electrode alone or in combination with one or more of the coil electrodes 28, 36, or 38, for defibrillation shocking purposes, The housing 40 further includes a connector 41 having a plurality of terminals 42, 43, 44, 46, 48, 52, 54 56, and 58 (shown schematically and, for convenience, the names of the electrodes to which they are connected are shown next to corresponding terminals). As such, in order to achieve right atrial sensing and stimulation, the connector 41 includes at least one right atrial tip terminal (RA TIP) 42 adapted for connection to the atrial tip electrode 22. The connector 41 may also include a right atrial ring terminal (RA RING) for connection to the right atrial ring electrode 23.

To achieve left chamber sensing, pacing, and/or shocking, the connector 41 may include a left ventricular tip terminal (LV TIP) 44, a left ventricular ring terminal (LV RING) 25, a left atrial ring terminal (LA RING) 46, and a left atrial shocking coil terminal (LA COIL) 48, that are adapted for connection to the left ventricular tip electrode 26, the left ventricular ring electrode 25, the left atrial ring electrode 27, and the left atrial coil electrode 28, respectively.

To support right ventricular sensing, pacing, and/or shocking, the connector 41 may further include a right ventricular tip terminal (RV TIP) 52, a right ventricular ring terminal (RV RING) 54, a right ventricular shocking coil terminal (RV COIL) 56, and an SVC shocking coil terminal (SVC COIL) 58, which are adapted for connection to the right ventricular (RV) tip electrode 32, the RV ring electrode 34, the RV coil electrode 36, and the SVC coil electrode 38, respectively.

A programmable microcontroller 60 controls the modes of stimulation therapy. The microcontroller 60 typically includes a microprocessor, or equivalent control circuitry, for controlling the delivery of stimulation therapy, and may include RAM or ROM memory, logic and timing circuitry, state machine circuitry, and/or I/O circuitry. The microcontroller 60 may have the ability to process or monitor various input signals (data) as controlled by a program code stored in a designated block of memory. The microcontroller 60 may further include timing control circuitry 79 which may be used to control timing of the stimulation pulses such as, e.g., pacing rate, atrio-ventricular (AV) delay, atrial interchamber (A-A) delay, and/or ventricular interchamber (V-V) delay.

An atrial pulse generator 70 and ventricular pulse generator 72 generate stimulation pulses for delivery by the right atrial lead 20, the right ventricular lead 30, and/or the coronary sinus lead 24 via a switch 74. The atrial pulse generator 70 and the ventricular pulse generator 72 are generally controlled by the microcontroller 60 via appropriate control signals 76 and 78, respectively, to trigger or inhibit the stimulation pulses.

The switch 74 includes a plurality of switches for connecting the desired electrodes to the appropriate I/O circuits, thereby providing complete electrode programmability. The switch 74, in response to a control signal 80 from the microcontroller 60, determines the polarity of the stimulation pulses (e.g., unipolar, bipolar, cross-chamber, and the like) by selectively closing the appropriate combination of switches. Atrial sensing circuits 82 and ventricular sensing circuits 84 may also be selectively coupled to the right atrial lead 20, coronary sinus lead 24, and the right ventricular lead 30 through the switch 74, for detecting the presence of cardiac activity in each of the four chambers of the heart.

The outputs of the atrial sensing circuit 82 and ventricular sensing circuits 84 may be connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, may receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84. For arrhythmia detection, the IMD 10 includes an arrhythmia detector 77 that utilizes the atrial and ventricular sensing circuits 82 and 84 to sense cardiac signals, for determining whether a rhythm may be physiologic or pathologic.

Cardiac signals are also applied to the inputs of a data acquisition system 90 which is depicted as an analog-to-digital (A/D) converter for simplicity of illustration. The microcontroller 60 may further be coupled to a memory 94 by a suitable data/address bus 96, wherein the programmable operating parameters used by the microcontroller 60 are stored and modified, as required, so as to customize the operation of the IMD 10 to suit the needs of particular patients. The IMD 10 may additionally include a power source, illustrated as a battery 110, for providing operating power to all the circuits of FIG. 2. For the IMD 10 employing shocking therapy, the battery 110 operates at low current drains for long periods of time, preferably less than 10 uA, and also be capable of providing high-current pulses when the patient requires a shock pulse, preferably in excess of 2 A, at voltages above 2 V, for periods of 10 seconds or more. The battery 110 preferably has a predictable discharge characteristic such that elective replacement time can be detected. A physiologic sensor 108 detects motion of the IMD and thus, patient to determine an amount of activity.

The IMD 10 includes an impedance measuring circuit 112 which is enabled by the microcontroller 60 by control signal 114. The uses for an impedance measuring circuit 112 include, but are not limited to, lead impedance surveillance during the acute and chronic phases for proper lead positioning or dislodgement; detecting operable electrodes and automatically switching to an operable pair in case dislodgement should occur; measuring respiration or minute ventilation; measuring thoracic impedance for determining shock thresholds; detecting when the device has been implanted; measuring stroke volume; detecting opening of heart valves, and so on.

The IMD 10 may be used as an implantable cardioverter defibrillator (ICD) device by detecting the occurrence of an arrhythmia, and automatically applying an appropriate electrical stimulation or shock therapy to the heart aimed at terminating the detected arrhythmia. To achieve the previously specified goal, the microcontroller 60 further controls a shocking circuit 116 by way of a control line 118. The shocking circuit 116 includes charge storage members, such as one or more capacitors. The charge storage members are charged by the battery 110 before delivering stimulating energy such as high energy shocks (e.g., 10 Joules, 20 Joules, 35 Joules). The charge storage members deliver the stimulating energy over positive and negative lines 55 and 57. The switch 74 includes a switch network 61 that is electrically disposed between the positive and negative lines 55 and 57, and the appropriate output terminals 42, 43, 44, 46, 48, 52, 54, 56, and 58 of the connector 41. The switch network 61 includes a collection of switches arranged in an H-bridge architecture, that change between open and closed states to disconnect and connect the charge storage members and the desired output terminals of the connector 41.

Figure 3:
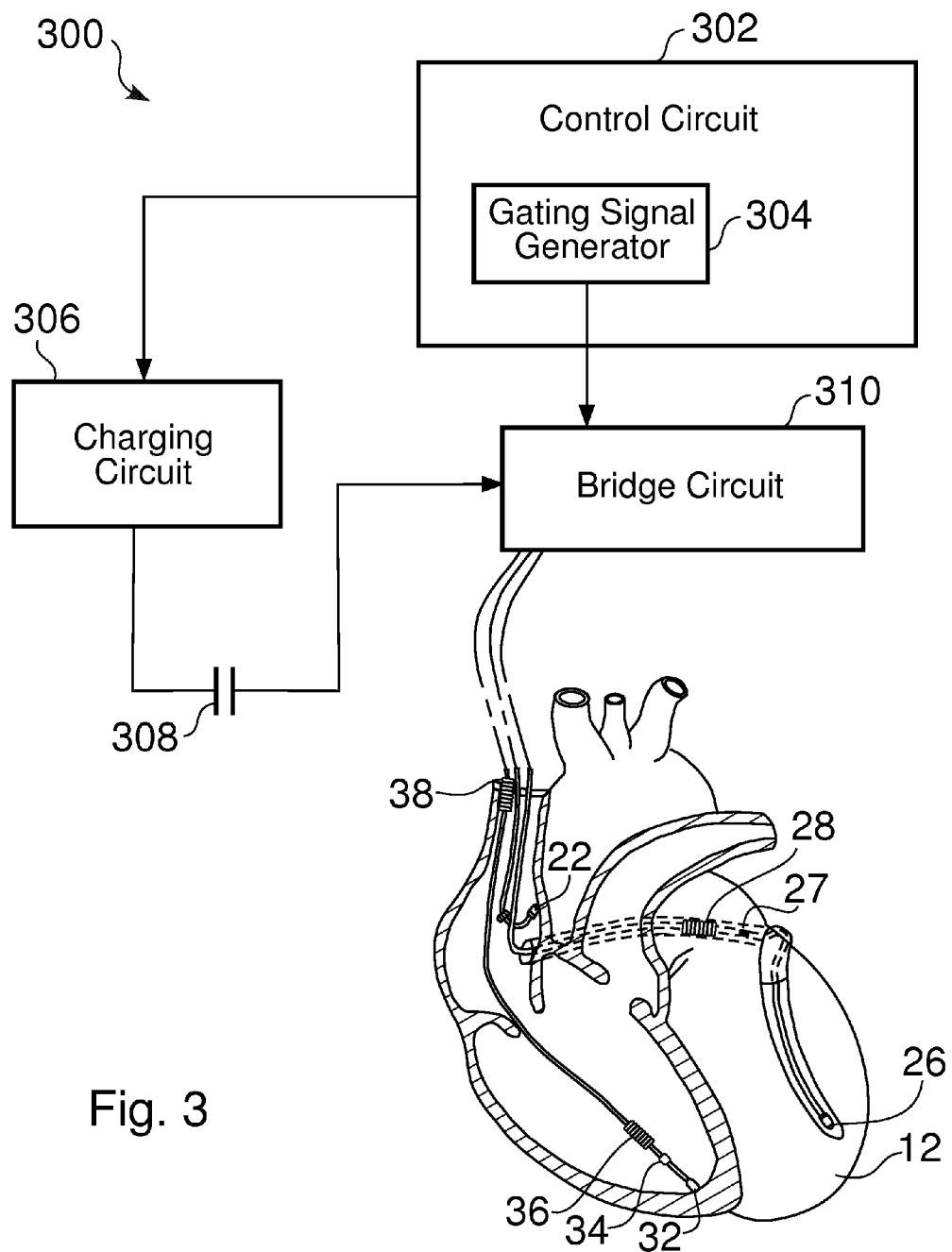
FIG. 3 is a simplified block diagram of a portion of an IMD for delivering high energy shocks in accordance with an embodiment.

FIG. 3 is a simplified block diagram of a portion of an ND 300 for delivering cardioversion and defibrillation high energy shocks in accordance with an embodiment. The IMD 300 includes a control circuit 302, a gating signal generator 304, a charging circuit 306, charge storage capacitors 308, and a bridge circuit 310. The control circuit 302 controls cardiac defibrillation operation. The control circuit 302 may generate commands for other components used in connection with cardioversion or defibrillation modes of operation based on programmed instructions. For example, the control circuit 302 monitors the heart action and, determines when a tachyarrhythmic condition is occurring. The control circuit 302 causes the charging circuit 306 to charge up storage capacitors 308 up to a programmed setting. For example the storage capacitors 308 may be charged up to 800 volts, In an embodiment, the storage capacitors 308 may be a combination of multiple capacitors to store very high charge (e.g., 20 Joules, 30 Joules, 35 Joules). Alternatively, a bank of capacitors or other energy storage devices may be used. When the charging cycle is complete, the control circuit 302 causes the gating signal generator 304 to direct the bridge circuit 310 to connect a predetermined combination of electrodes to the storage capacitor 308 and discharge the predetermined energy to select electrodes 22, 26, 27, 28, 32, 34, 36, and 38. In one embodiment, three electrodes 28, 36, and 38 may be used for defibrillation. Alternatively, fewer or more than three electrodes may be used. In another embodiment, a left ventricular lead may be provided with one or multiple electrodes that operate as high energy discharge sites.

Figure 4:
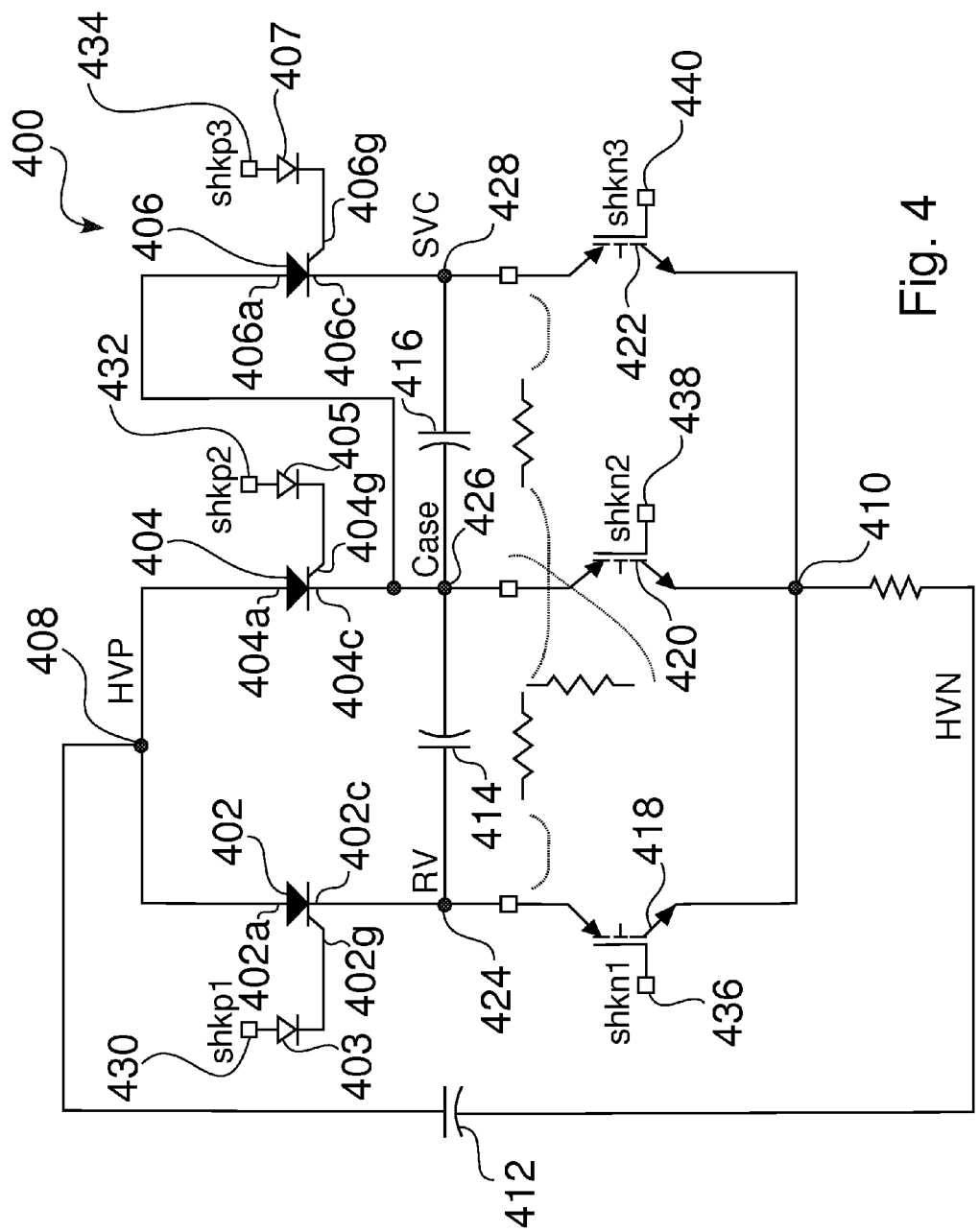
FIG. 4 is a high voltage switching circuit 400 formed in accordance with an embodiment.

FIG. 4 illustrates a circuit diagram of a high voltage switching and control circuit 400 for an implantable medical device (IMD) formed in accordance with an embodiment. The circuit 400 includes a HVP node 408 configured to receive a positive high voltage signal from a high energy storage source, such as the storage capacitors 308 (FIG. 3). The circuit 400 includes a high voltage negative (HVN) node 410 configured to receive a negative high voltage signal from the high energy storage source (e.g., storage capacitors 308). First, second and third output terminals 424, 426 and 428 are configured to be connected to electrodes for delivering high voltage energy to a patient. For example, the output terminal 424 may be connected to an RV electrode 36 (FIG. 1), the output terminal 426 may be connected to a case electrode (e.g., the CASE 43), and the output terminal 428 may be connected to an SVC electrode 38. Alternatively, the output terminal 426 may be connected to an LV electrode (e.g., 25), and the output terminal 428 may be connected to an LA electrode 28. Alternatively, the output terminal 426 may be connected to a combination of electrodes (e.g., LV electrodes 26 and 25), and the output terminal 428 may be connected to the case electrode (e.g., CASE 43).

The circuit 400 includes a collection of switches 402, 404, 406, 418, 420 and 422 arranged in a three-legged H-bridge. A first subset of the switches (e.g., 402, 404, and 406) is positioned on the positive high voltage (or "high") side of the output terminals 424, 426 and 428. A second subset of the switches (e.g., 418, 420 and 422) is positioned on the negative high voltage (or "low")side of the output terminals 424, 426 and 428. In the example of FIG. 4, the subset of switches (e.g., 402, 404, 406) on the positive high voltage side are silicon controlled rectifiers (SCRs), while the subset of switches (e.g., 418, 420, 422) on the negative high voltage side are insulated bipolar gate transistors (IGBTs). Pairs of switches (402, 418), (404,420) and (406, 422) are arranged, with opposite sides of a corresponding output terminal.

The Silicon Controlled Rectifier is a semiconductor device that is a member of a family of control devices known as Thyristors. The SCR is a three-lead device with an anode and a cathode (as with a standard diode) plus a third control lead, also referred to as a gate terminal. The SCR switches 402, 404, and 406, include anodes 402a, 404a and 406a, cathodes 402c, 404c and 406c, and gating terminals 402g, 404g and 406g. As the name implies, an SCR is a rectifier which may be controlled or "triggered" to the "ON" state by applying a small current to the lead for the gate. Once gated ON, the gating or trigger signal may be removed and the SCR switch will remain in a conducting state as long as current flows through the SCR switch. In the example of FIG. 4, the anode 402a of the SCR switch 402 is connected to the HVP node 408 and the cathode 402c is connected to the output terminal 424. The anode 404a of the SCR switch 404 is connected to the HVP node 408 and the cathode 404c is connected to the output terminal 426. The anode 406a of the SCR switch 406 is connected to the cathode node 404c of the SCR switch 404 and the cathode 406c is connected to the output terminal 428. The gating terminals 402g, 404g, and 406g are connected to control signal inputs 430, 432, and 434. Optionally, isolation diodes 403, 405 and 407 may be provided between the gating terminals 402g, 404g, and 406g and the control signal inputs 430, 432, and 434, respectively. The isolation diodes 403, 405 and 407 isolate the control signal inputs 430, 432 and 434 (and thus the control circuit) from the high energy that is delivered through the SCR switches 402, 404, 406 during defibrillation or cardioversion. A control circuit delivers gating signals at the control signal inputs 430, 432 and 434. The gating signals pass through the isolation diodes 403, 405 and 407 to the gating terminals 402g, 404g and 406g to turn ON the SCR switches 402, 404 and 406. By way of example, the gating signals may be delivered from the gating signal generator 304 it the control circuit 302 of FIG. 3.

The IGBT switches 418, 420 and 422 have collectors 418c, 420c, and 422c, emitters 418e, 420e and 422e, and gates 418g, 420g and 422g. The collectors 418c, 420c, and 422c are connected to corresponding output terminals 424, 426 and 428. The emitters 418e, 420e, and 422e are connected to the HVN node 410. The gates 418g, 420g, and 422g are connected to control signal inputs 436, 438, and 440. Optionally, isolation components may be provided between the bases 418g, 420g, and 422g and the control signal inputs 436, 438, and 440. The control circuit delivers gating signals at the control signal inputs 436, 438, and 440 to turn ON and OFF the IGBT switches 418, 420 and 422. By way of example, the gating signals may be delivered from the gating signal generator 304 in the control circuit 302 of FIG. 3.

Also, the circuit 400 includes an electromagnetic interference (EMI) protection capacitor 414 between the first and the second output terminals 424, 426. The circuit 400 includes an EMI protection capacitor 416 between the second and third output terminals 426, 428. The EMI protection capacitor 414 creates a high frequency "short" connection between the case 426 and the node 424. The EMI protection capacitor 416 creates a high frequency "short" connection between the case 426 and the node 428.

The circuit 400 is designed to enable delivery of positive or negative high voltage energy from select combinations of the two, three or more output terminals 424, 426 and 428 based on the mode of operation and the desired shock vector(s). In the example of FIG. 4, the circuit 400 may deliver high voltage energy of a single common polarity (e.g. positive) from output terminals 426 and 428, while high voltage energy of an opposite polarity (e.g., negative) is delivered from the third output terminal 424 (e.g., for shock vectors RV-SVC and RV-Case). In this example, shocking vectors are created between the SVC electrode 38 (FIG. 1) and the RV electrode 36 and between the CASE electrode 43 and the RV electrode 36. In this example, the SCR switches 404 and 406 are connected to the HVP node 408 and to first and second output terminals 426 and 428. Optionally, the SCR switches 404 and 406 can remain in the OFF position.

The SCR switches 404 and 406 are connected in series whereby the anode 406a of SCR switch 406 is directly connected to the cathode 404c of SCR switch 404 at a position upstream of the output terminal 426.

A control circuit (e.g., 302 in FIG. 3) is connected to the control signal inputs 430, 432, 434, 436, 438 and 440. When delivering high energy simultaneously or concurrently along multiple shock vectors, the control circuit 302 temporally offsets the first and second gating signals to turn ON the first and second SCR switches in a serial delayed manner. More specifically, the control circuit 302 supplies the gating signal (at gating terminal 406g) to the SCR switch 406 first, before the control circuit 302 supplies the gating signal (at gating terminal 404g) to the SCR switch 404. By staggering the deliver times of the gating signals, the control circuit 302 is able to turn ON the SCR switch 406, before turning ON the SCR switch 404. When the SCR switch 406 is initially turned ON, but before the SCR switch 404 is turned ON, no current flows to SCR switch 406, hence no high energy is delivered to the patient. Once the SCR switch 404 is turned ON, current begins to flow to both of the SCR switches 404 and 406 concurrently or at the same time.

Figure 5:
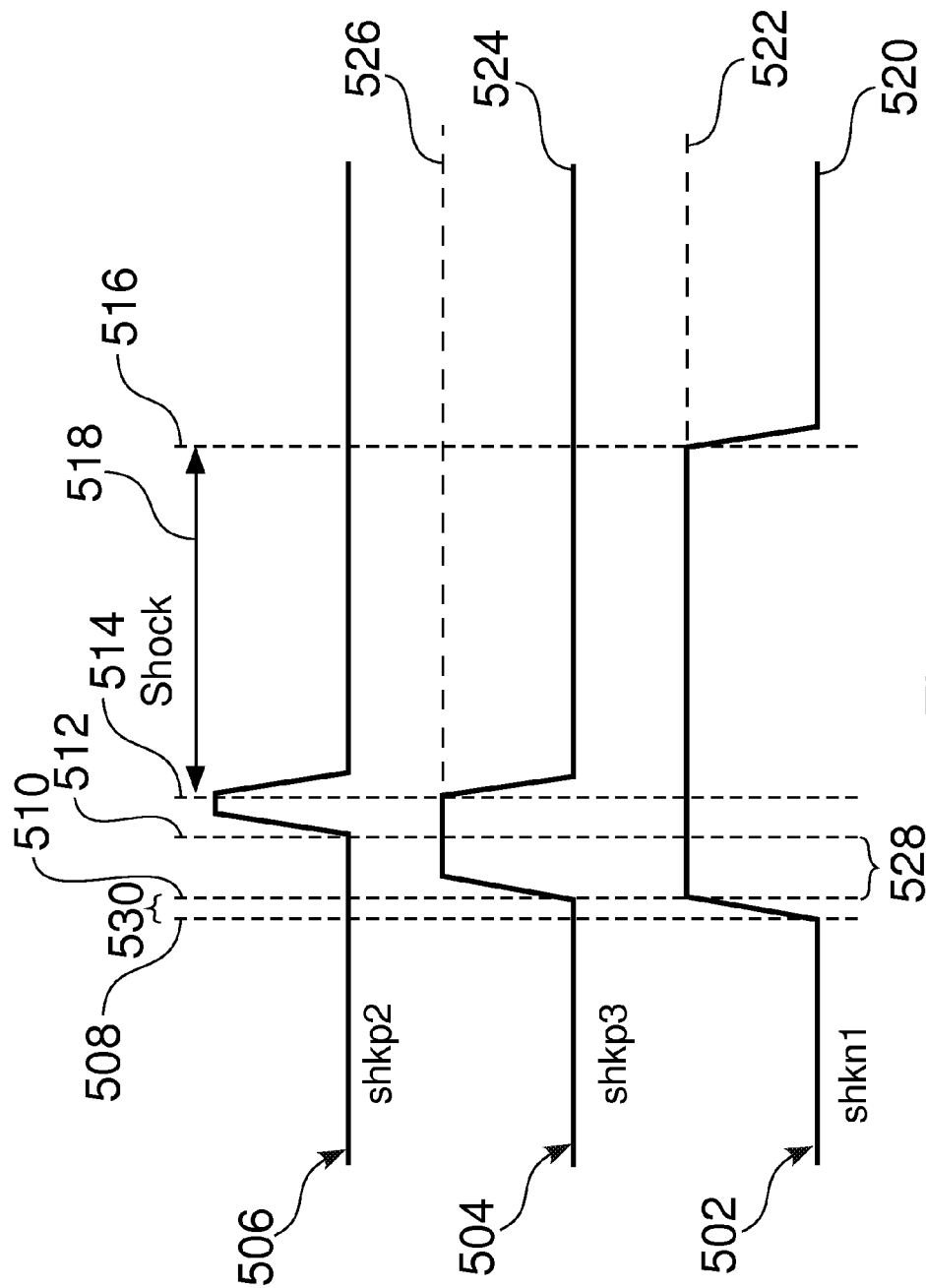
FIG. 5 illustrates a timing chart for exemplary gating signals to control the operation of the switching circuit in accordance with an embodiment.

FIG. 5 illustrates a relative timing of exemplary gating signals to control the operation of the high voltage switching circuit 400 in accordance with an embodiment. The switches 404, 406, 418 in the circuit 400 are controlled by the gating signals 506, 504, 502 depicted in FIG. 5. The control circuit delivers gating signals at the control signal inputs 432, 434 and 430. A trigger gating signal for an IGBT switch may represent a voltage signal, where in the case of an SCR switch, a trigger gating signal may represent a current signal.

The control circuit 302 generates the first gating signal 502 prior to turning ON the SCR switches 404 and 406. The first gating signal 502 changes from a first signal level 520 to a second signal level 522. Because of capacitive and other effects, the control circuit 302 may not instantaneously switch from the first signal level 520 to the second signal level 522 and vice versa. As such, a short finite time is typically permitted to allow for a signal level change to be achieved. For example, the control circuit 302 may provide a signal at the first signal level 520 until time 508. At time 508, the control circuit 302 outputs the second signal level 522, which is achieved at a later time 510. A transition time 530 occurs from time 508 to time 510 during which the signal level transitions between the two signal levels 520 and 522.

At time 510, the IGBT switch 418 changes state from open (OFF) to closed (ON). The closing of switch 418 allows the HNV to create a potential difference across output terminal 424 and HVP node 408. The potential difference, considering some loss of signal level, may be the same as the potential difference across charge storage source 412, The negative potential difference determines the direction of a shocking vector.

Also, at time 510, the control circuit 302 generates the second gating signal 504. The second gating signal 504 changes from a first signal level 524 to the second signal level 526. After the gating signal 504 achieves the second signal level 526, the SCR switch 406 changes state from open (OFF) to closed (turned ON).

Next, at time 512, the control circuit 302 generates the second gating signal 506. The control circuit 302 temporally offsets gating signals 504 and 506 by an offset 528 to turn ON the switches 406 and 404 in a serial delayed manner. By staggering the deliver times of the gating signals 504 and 506, the control circuit 302 is able to turn ON the switch 406, before turning ON the switch 404. When the switch 406 is initially turned ON, but before the switch 404 is turned ON, no current flows to switch 406. Once the switch 404 is turned ON, the potential developed across the HVP node 408 and the output terminal 424 forces the current to flow from the HVP node 408 towards the output terminal 424. The current flows from the SCR switches 404 and 406 at the same time providing the shock to the heart along multiple concurrent vectors. The shock is provided for a duration 518 extending from time 514 to time 516 under the control of the control circuit 302. When multiple shock vectors RV-SVC and RV-Case are used, the SCR switch 404 and 406 cause a common polarity HV signal to be delivered to the SVC and CASE electrodes 38 and 43. Alternatively, when only a simple shock vector RV-Can is used, the SCR switch 406 remains OFF and only the SCR switch 404 is turned ON, thereby delivering an HV signal to the CASE electrode 43 and maintaining the SVC electrode 38 inactive.

Figure 6A:
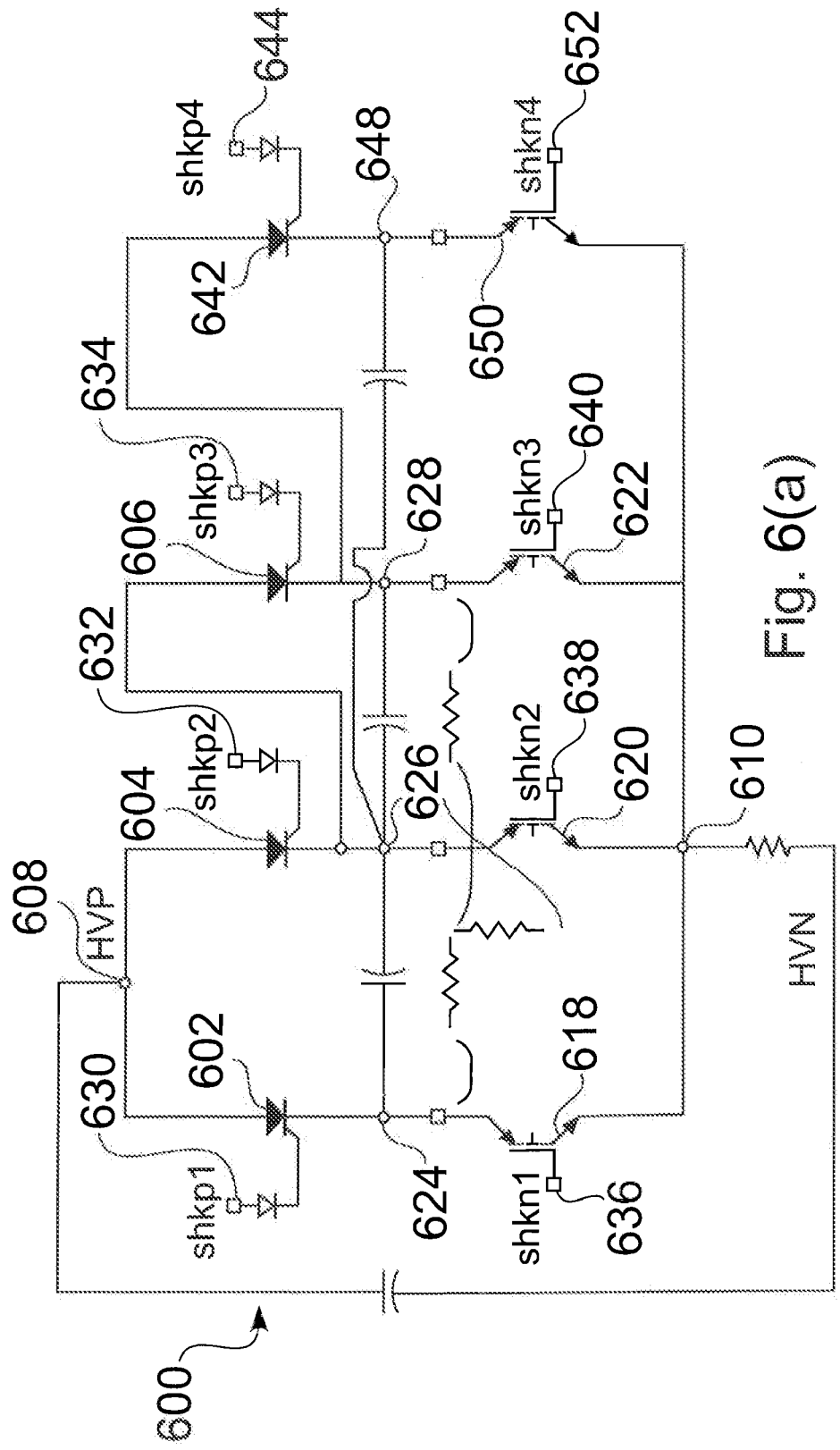
FIG. 6(a) illustrates an alternate embodiment of a high voltage switching circuit.
Figure 6B:
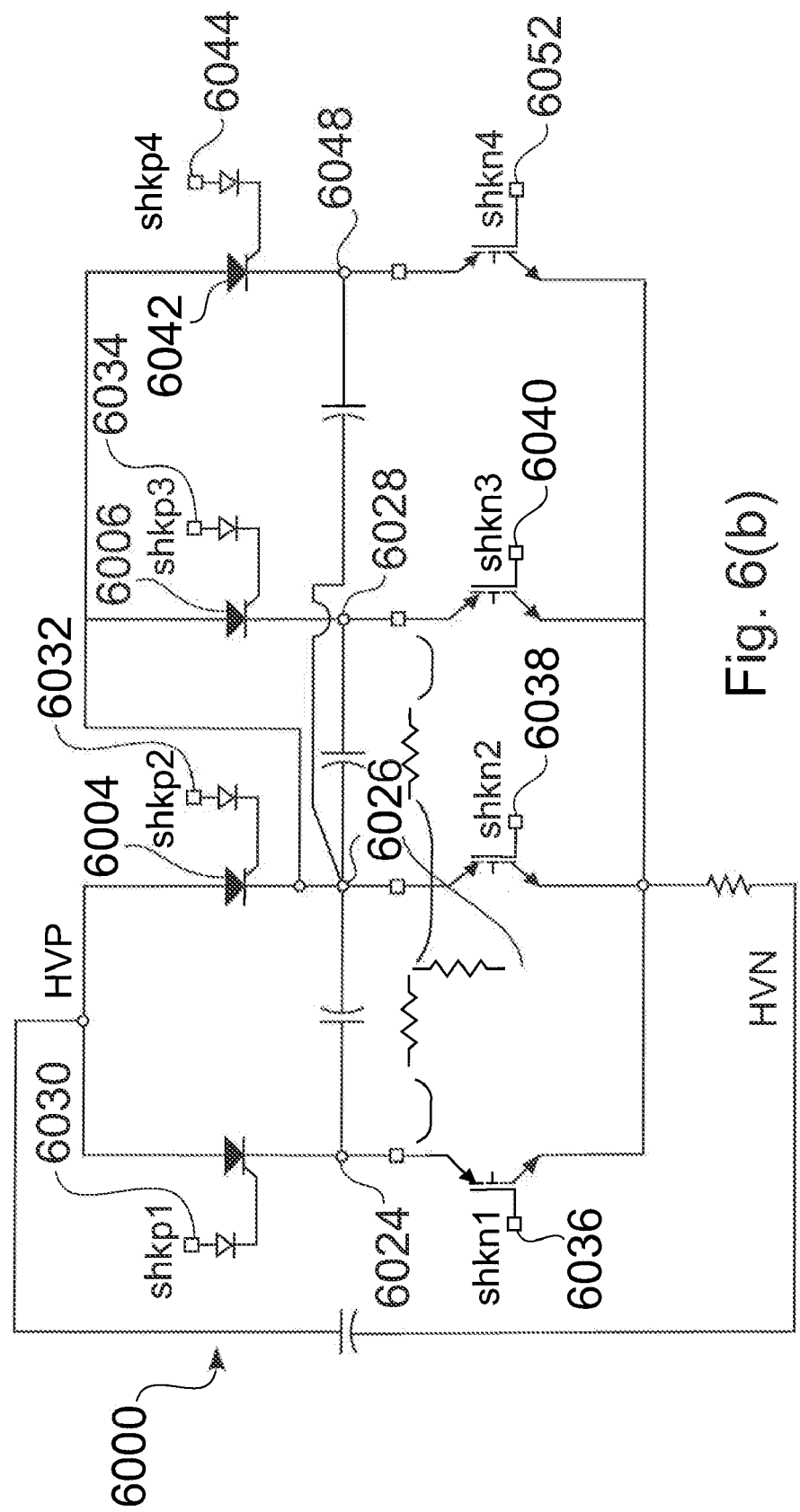
FIG. 6(b) illustrates an alternate embodiment of a high voltage switching circuit.

FIG. 6(*a*) illustrates an alternate embodiment of the high voltage switching circuit 400. The circuit 600 includes a high voltage positive (HVP) node 608 configured to receive a positive high voltage signal from a high energy storage source, such as the storage capacitors 308 (FIG. 3). The circuit 600 includes a high voltage negative (HVN) node 610 configured to receive a negative high voltage signal from the high energy storage source (e.g., storage capacitors 308). First, second, third, and fourth output terminals 624, 626, 628, 648 are configured to be connected to electrodes for delivering high voltage energy to a patient. For example, the output terminal 624 may be connected to an RV electrode 36 (FIG. 1), the output terminal 626 may be connected to a case electrode (e.g., the CASE 43), the output terminal 628 may be connected to an SVC electrode 38, and output terminal 648 may be connected to an LV electrode. Alternatively, the output terminal 626 may be connected to an RA electrode 28, the output terminal 628, and 648 may be connected to an LV electrode with multiple shocking sites.

The circuit 600 includes a collection of switches 602, 604, 606, 642, 618, 620, 622, 650 arranged in a four-legged H-bridge. A first subset of the switches (e.g., 602, 604, 606, 642) is positioned on the positive high voltage (or "high") side of the output terminals 624, 626, 628 and 648. A second subset of the switches (e.g., 618, 620, 622, 650) is positioned on the negative high voltage (or "low") side of the output terminals 624, 626, 628, 648. In the example of FIG. 6(*a*), the subset of switches (e.g., 602, 604, 606, and 642) on the positive high voltage side is SCR, while the subset of switches (e.g., 618, 620, 622, and 650) on the negative high voltage side is IBGT. Pairs of switches (602, 618) (604,620), (606, 622), and (642, 650) are arranged in parallel, with opposite sides of a corresponding output terminal.

The SCR switches 604, 606, and 642 are connected in series whereby the anodes of SCR switch 606 and 642 are directly connected to the cathodes of SCR switch 604 and 606 respectively, at a position upstream of the output terminal 626 and 628 respectively.

A control circuit (e.g., 302 in FIG. 3) is connected to the control signal inputs 630, 632, 634, 644, 636, 638, 640, and 652. When multiple, simultaneous or concurrently shock vectors are utilized, the control circuit 302 delivers first, second, and third gating signals to turn ON the SCR switches 604, 606, and 642 respectively. When delivering high energy simultaneously or concurrently along multiple shock vectors, the control circuit 302 temporally offsets the first, second, and third gating signals to turn ON the first, second, and third SCR switches (604, 606, and 642) in a serial delayed manner. More specifically, the control circuit 302 supplies the gating signal to the SCR switch 642 first, before the control circuit 302 supplies the gating signal to the SCR switch 606. The control circuit 302 supplies the gating signal to the SCR switch 606 next, before the control circuit 302 supplies the gating signal to the SCR switch 604. By staggering the deliver times of the gating signals, the control circuit 302 is able to turn ON the SCR switch 642, before turning ON the SCR switch 606, before turning ON the SCR switch 604. When the SCR switches 642 and 606 are initially turned ON, but before the SCR switch 604 is turned ON, no current flows to SCR switches 642 and 606, hence no high energy is delivered to the patient. Once the SCR switch 604 is turned ON, current begins to flow to the SCR switches 604, 606, and 642 at the same time.

FIG. 6(*b*) illustrates another alternate embodiment of the High voltage switching circuit 400. The circuit 6000 includes first, second, third, and fourth output terminals 6024, 6026, 6028, and 6048 configured to be connected to electrodes for delivering high voltage energy to a patient. Additionally, the circuit 6000 illustrates SCR switches (6004, 6006 and 6042) connected together in a combination of serial and parallel setup.

The SCR switches 6004 and 6006 are connected in series whereby the anode of SCR switch 6006 is directly connected to the cathode of SCR switch 6004 at a position upstream of the output terminal 6026. The SCR switches 6006 and 6042 are connected in parallel whereby the anodes of SCR switch 6006 and 6042 are directly connected to the cathode of SCR switch 6004 at a position upstream of the output terminal 6026.

A control circuit (e.g., 302 in FIG. 3) is connected to the control signal inputs 6030, 6032, 6034, 6044, 6036, 6038, 6040, and 6052. When multiple, simultaneous or concurrently shock vectors are utilized, the control circuit 302 delivers first, second, and third gating signals to turn ON the SCR switches 6004, 6006, and 6042 respectively. When delivering high energy simultaneously or concurrently along multiple shock vectors, the control circuit 302 temporally offsets the first from the second and third gating signals to turn ON the first SCR switch 6004 in a serial delayed manner to second and third SCR switches 6006, 6042. However, the SCR switches 6006 and 6042 may be turned ON in a parallel manner.

More specifically, the control circuit 302 supplies the gating signal to the SCR switches 6006 and 6042 first, before the control circuit 302 supplies the gating signal to the SCR switch 6004. By staggering the deliver times of the gating signals, the control circuit 302 is able to turn ON the SCR switches 6006 and 6042 before turning ON the SCR switch 6004. When the SCR switches 6042 and 6006 are initially turned ON, but before the SCR switch 6004 is turned ON, no current flows to SCR switches 6042 and 6006, hence no high energy is delivered to the patient.

Alternatively, only one SCR switch of the two SCR switches 6006, 6042 may be turned ON.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the subject matter disclosed herein without departing from its scope. While the dimensions, types of materials and coatings described herein are intended to define the parameters of the subject matter disclosed herein, they are by no means limiting and are exemplary embodiments. Many other embodiments will be apparent to those of skill in the art upon reviewing the above description. The scope of the subject matter disclosed herein should, therefore, be determined with reference to the appended claims, along with the full scope of equivalents to which such claims are entitled. In the appended claims, the terns "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A high voltage switching and control circuit for an implantable medical device (IMD), comprising:
   a high voltage (HV) node, the HV node being one of either a high voltage positive (HVP) node adapted to receive a positive high voltage signal from a high energy storage source, or a high voltage negative (HVN) node adapted to receive a negative high voltage signal from a high energy storage source;
   first and second output terminals adapted to be connected to electrodes for delivering high voltage energy;
   first and second Silicon Controlled Rectifiers (SCR) switches connected in series with one another and connected to the HV node, the first and second SCR switches connected to the first and second output terminals respectively, the first and second SCR switches connecting the HV node to the first and second output terminals respectively;
   the first and second SCR switches having gating terminals; and
   a control circuit connected to the gating terminals programmed to deliver first and second gating signals to turn ON the first and second SCR switches, respectively, the control circuit temporally offsetting the first and second gating signals to turn ON the first and second SCR switches in a serial delayed manner such that the second switch is turned ON before the first switch and no current flows to the second switch before the first switch is turned ON.

2. The circuit of claim 1, wherein the HV node is a HVP node, the first output terminal represents a case terminal configured to be connected to a case electrode, the first SCR switch being connected between the HVP node and the case terminal, the second SCR switch connected in series with an output of the first SCR switch at a point between the first SCR switch and the case terminal, the control circuit turning ON the second SCR switch before turning ON the first SCR switch, 3. The circuit of claim 1, wherein the second output terminal represents a Superior Vena Cava (SVC) terminal configured to be connected to a SVC electrode.

4. The circuit of claim 1, further comprising a third output terminal, wherein the first, second and third output terminals are configured to be connected to a case electrode, an Superior Vena Cava (SVC) electrode and a Right Ventricle (RV) electrode, respectively.

5. The circuit of claim 1, further comprising additional switches and a third output terminal, the output terminals, first and second SCR switches and the additional switches being arranged in an H-bridge having three output terminals.

6. The circuit of claim 1, further comprising:
   a first, a second, and a third Isolated Gate Bipolar Transistor (IGBT) switches and a third output terminal, wherein the HV node is a HVN node and wherein the HVN node and the first, second and third IGBT switches are connected to the first, second and third output terminals respectively.

7. The circuit of claim 6, wherein the control circuit is connected to the third IGBT switch, the control circuit closing the third IGBT switch before closing the first and second SCR switches.

8. The circuit of claim 1, wherein the control circuit controls the serial delayed manner for turning ON the first and second SCR switches such that a shocking voltage is not delivered to a patient through either of the first and second SCR switches until both of the first and second SCR switches are turned ON.

9. The circuit of claim 1, further comprising a third output terminal, wherein the first, second and third output terminals are configured to be connected to first, second and third electrodes that collectively define first and second shocking vectors through the heart.

10. The circuit of claim 1, further comprising isolation diodes provided between the control circuit and gating terminals of the first and second SCR switches.

11. The circuit of claim 1, further comprising a third SCR switch, the first and third SCR switches having cathodes coupled to a common node connected.

12. A method for operating a high voltage switching and control circuit in an implantable medical device (IMD), the circuit having i) high voltage positive (HVP) and negative (HVN) nodes; ii) first, second and third output terminals adapted to be connected to electrodes for delivering high voltage energy, iii) multiple switches connecting the HVP and HVN nodes to the first, second and third output terminals, the switches including at least first and second Silicon Controlled Rectifiers (SCR) switches connected in series with one another and connected to one of the HVP and HVN nodes, the first and second SCR switches having gating terminals, an input of the second SCR switch being connected to an output of the first SCR switch, the method comprising:

providing high voltage signals using a high energy storage source at the HVP node and the HVN node;

delivering a first gating signal to the gating terminal of the second SCR switch to turn ON the second SCR switch;

delivering a second gating signal to the gating terminal of the first SCR switch to turn ON the first SCR switch;

offsetting a delivery timing of the first and second gating signals in a serial delayed manner such that the first gating signal turns ON the second SCR switch before the second gating signal turns ON the first SCR switch; and delivering high voltage energy to the first and second output terminals concurrently in response to the second gating signal turning ON the first SCR switch.

13. The method of claim 12, further comprising operably connecting the first SCR switch to a case terminal, the second SCR switch to an Superior Vena Cava (SVC) terminal and the third SCR switch to an Right Ventricle (RV) terminal, the delivering operation providing high voltage energy along at least two shock vectors through the heart.

14. The method of claim 13, further comprising connecting at least first, second and third Isolated Gate Bipolar Transistor (IGBT) switches to the HVN node.

15. The method of claim 14, wherein the first IGBT switch is connected to the third output terminal, the method further comprising turning ON the first IGBT switch before turning ON the first and second SCR switches.

16. The method of claim 12, wherein the first output terminal represents a case terminal configured to be connected to a case electrode, the first SCR switch being connected between the HVP node and the case terminal, the second SCR switch connected in series with an output of the first SCR switch at a point between the first SCR switch and the case terminal, the method including turning ON the second SCR switch before turning ON the first SCR switch.

17. A high voltage switching and control circuit for an implantable medical device (IMD), comprising:

a high voltage (HV) node, the HV node being one of either a high voltage positive (HVP) node adapted to receive a positive high voltage signal from a high energy storage source, or a high voltage negative (HVN) node adapted to receive a negative high voltage signal from a high energy storage source;

first and second output terminals adapted to be connected to electrodes for delivering high voltage energy;

first and second Silicon Controlled Rectifiers (SCR) switches connected in series with one another and connected to the HV node, the first and second SCR switches connected to the first and second output terminals respectively, the first and second SCR switches connecting the HV node to the first and second output terminals respectively;

the first and second SCR switches having gating terminals; and a control circuit connected to the gating terminals programmed to deliver first and second gating signals to turn ON the first and second SCR switches, respectively, the control circuit temporally offsetting the first and second gating signals to turn ON the first and second SCR switches in a serial delayed manner such that a shocking voltage is delivered to a patient through both the first and second SCR switches only when both of the first and second SCR switches are turned ON.

18. The circuit of claim 17, wherein the HV node is a HVP node, the first output terminal represents a case terminal configured to be connected to a case electrode, the first SCR switch being connected between the HVP node and the case terminal, the second SCR switch connected in series with an output of the first SCR switch at a point between the first SCR switch and the case terminal, the control circuit programmed to turn ON the second SCR switch before turning ON the first SCR switch.

19. The circuit of claim 17, further comprising a third output terminal, wherein the first, second and third output terminals are configured to be connected to a case electrode, an Superior Vena Cava (SVC) electrode and a Right Ventricle (RV) electrode, respectively.

\* \* \* \* \*